Figure 2:
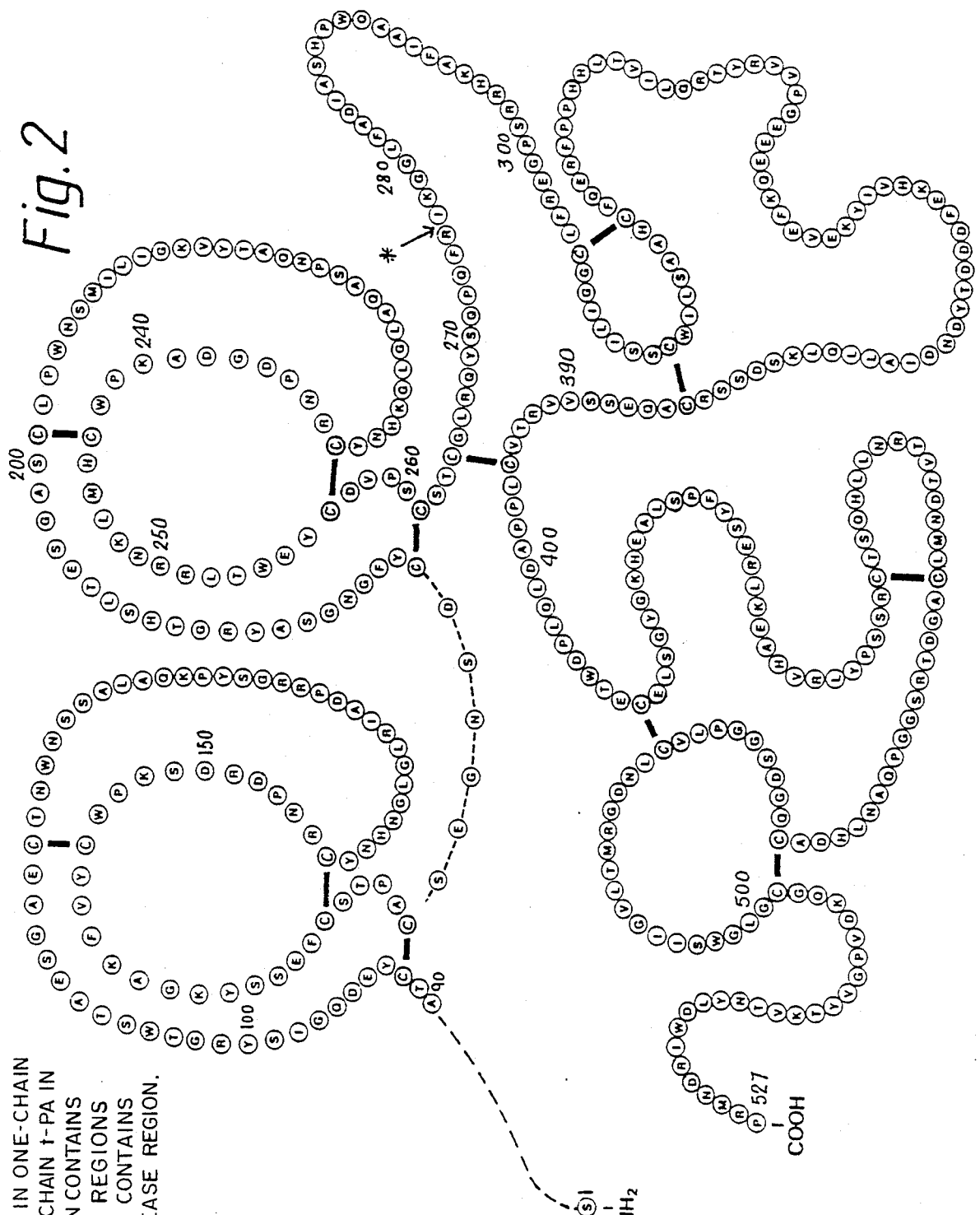

United States Patent [19]

Whittle

[11] Patent Number: 4,839,169

[45] Date of Patent: Jun. 13, 1989

[54] SYNERGISTIC COMBINATION OF T-PA AND PROSTACYCLIN

[75] Inventor: Brendan J. R. Whittle, Beckenham, England

[73] Assignee: Burroughs Wellcome Co., Research Triangle Park, N.C.

[21] Appl. No.: 81,242

[22] Filed: Aug. 4, 1987

[30] Foreign Application Priority Data

Aug. 5, 1986 [GB] United Kingdom ................ 8619098

[51] Int. Cl.⁴ .................. A61K 37/547; A61K 31/557
[52] U.S. Cl. .................................. 424/94.3; 424/94.64; 424/94.63; 435/226; 435/212; 514/822; 514/531; 514/573
[58] Field of Search ................ 424/94.3, 94.63, 94.64; 560/503; 435/226, 212; 514/822, 531, 573

[56] References Cited

U.S. PATENT DOCUMENTS

| | | | |
|---|---|---|---|
| 4,158,667 | 6/1979 | Axen | 260/413 |
| 4,338,323 | 7/1983 | Johnson et al. | 424/285 |
| 4,539,333 | 9/1985 | Moncada | 514/469 |
| 4,632,919 | 12/1986 | Spillert et al. | 514/275 |

FOREIGN PATENT DOCUMENTS

| | | | |
|---|---|---|---|
| 0112122 | 6/1984 | European Pat. Off. | 424/94.6 |
| 8703488 | 6/1985 | PCT Int'l Appl. | |

OTHER PUBLICATIONS

J. Pharmac. Exp. Therap., 222 (3), 544–9, (1982).
Thromb Res, 29, 655–60, (1983).
J Cardiovasc. Pharmac., 7, 739–46, (1985).
Ubatuba et al., Chem Abs, 91: 69052q, 1979.
Schumacher et al., Chem Abs. 103: 98516r, 1985.
Gorog et al., Chem Abs., 106: 13536m, 1986 (pub date).
Marx, Science, 196, Jun. 1977, pp. 1072–1075.
Collen et al., Chem Abs, 98 (15): 119425f, 1983.

*Primary Examiner*—Howard E. Schain
*Assistant Examiner*—Jeff P. Kushan
*Attorney, Agent, or Firm*—Donald Brown

[57] ABSTRACT

A combination of t-PA and a prostaglandin of use in removing or inhibiting the formation of a blood clot in a mammal.

11 Claims, 3 Drawing Sheets

Ser Tyr Gln Val Ile Cys Arg Asp Glu Lys Thr Gln Met Ile Tyr Gln Gln His Gln Ser
1
Trp Leu Arg Pro Val Leu Arg Ser Asn Arg Val Glu Tyr Cys Trp Cys Asn Ser Gly

Arg Ala Gln Cys His Ser Val Pro Val Lys Ser Cys Ser Glu Pro Arg Cys Phe Asn
                                        50
Gly Gly Thr Cys Gln Gln Ala Leu Tyr Phe Ser Asp Phe Val Cys Gln Cys Pro Glu

Gly Phe Ala Gly Lys Cys Cys Glu Ile Asp Thr Arg Ala Thr Cys Tyr Glu Asp Gln

Gly Ile Ser Tyr Arg Gly Thr Trp Ser Thr Ala Glu Ser Gly Ala Glu Cys Thr Asn Trp
            100
Asn Ser Ser Ala Leu Ala Gln Lys Pro Tyr Ser Gly Arg Arg Pro Asp Ala Ile Arg

Leu Gly Leu Gly Asn His Asn Tyr Cys Arg Asn Pro Asp Arg Asp Ser Lys Pro Trp
                                                150
Cys Tyr Val Phe Lys Ala Gly Lys Tyr Ser Ser Glu Phe Cys Ser Thr Pro Ala Cys

Ser Glu Gly Asn Ser Asp Cys Tyr Phe Gly Asn Gly Ser Ala Tyr Arg Gly Thr His

Ser Leu Thr Glu Ser Gly Ala Ser Cys Leu Pro Trp Asn Ser Met Ile Leu Ile Gly Lys
                        200
Val Tyr Thr Ala Gln Asn Pro Ser Ala Gln Ala Leu Gly Leu Gly Lys His Asn Tyr

Cys Arg Asn Pro Asp Gly Asp Ala Lys Pro Trp Cys His Met Leu Lys Asn Arg Arg
                                                                    250
Leu Thr Trp Glu Tyr Cys Asp Val Pro Ser Cys Ser Thr Cys Gly Leu Arg Gln Tyr

Ser Gln Pro Gln Phe Arg Ile Lys Gly Gly Leu Phe Ala Asp Ile Ala Ser His Pro Trp

Gln Ala Ala Ile Phe Ala Lys His Arg Arg Ser Pro Gly Glu Arg Phe Leu Cys Gly
                                    300
Gly Ile Leu Ile Ser Ser Cys Trp Ile Leu Ser Ala Ala His Cys Phe Gln Glu Arg Phe

Pro Pro His His Leu Thr Val Ile Leu Gly Arg Thr Tyr Arg Val Val Pro Gly Glu Glu

Glu Gln Lys Phe Glu Val Glu Lys Tyr Ile Val His Lys Glu Phe Asp Asp Asp Thr
        350
Tyr Asp Asn Asp Ile Ala Leu Leu Gln Leu Lys Ser Asp Ser Ser Arg Cys Ala Gln

Glu Ser Ser Val Val Arg Thr Val Cys Leu Pro Pro Ala Asp Leu Gln Leu Pro Asp
                                            400
Trp Thr Glu Cys Glu Leu Ser Gly Tyr Gly Lys His Glu Ala Leu Ser Pro Phe Tyr

Ser Glu Arg Leu Lys Glu Ala His Val Arg Leu Tyr Pro Ser Ser Arg Cys Thr Ser

Gln His Leu Leu Asn Arg Thr Val Thr Asp Asn Met Leu Cys Ala Gly Asp Thr Arg
                        450
Ser Gly Gly Pro Gln Ala Asn Leu His Asp Ala Cys Gln Gly Asp Ser Gly Gly Pro

Leu Val Cys Leu Asn Asp Gly Arg Met Thr Leu Val Gly Ile Ile Ser Trp Gly Leu
                                                                500
Gly Cys Gly Gln Lys Asp Val Pro Gly Val Tyr Thr Lys Val Thr Asn Tyr Leu Asp

Trp Ile Arg Asp Asn Met Arg Pro
                527

FIG. 1

* SITE OF CLEAVAGE IN ONE-CHAIN t-PA TO GIVE TWO-CHAIN t-PA IN WHICH THE A-CHAIN CONTAINS THE TWO KRINGLE REGIONS AND THE B-CHAIN CONTAINS THE SERINE PROTEASE REGION.

SYNERGISTIC COMBINATION OF T-PA AND PROSTACYCLIN

The present invention relates to a combination of tissue plasminogen activator and a prostaglandin, to pharmaceutical formulations containing them, and to their use in human and veterinary medicine.

There exists a dynamic equilibrium between the enzyme system capable of forming blood clots, the coagulation system, and the enzyme system capable of dissolving blood clots, the fibrinolytic system, which maintains an intact patent vascular bed. To limit loss of blood from injury, blood clots are formed in the injured vessel. After natural repair of the injury, the superfluous blood clots are dissolved through operation of the fibrinolytic system. Occasionally, blood clots form without traumatic injury and may lodge in major blood vessels resulting in a partial or even total obstruction to blood flow. When this occurs in the heart, lung or brain, the result may be a myocardial infarction, pulmonary embolism or stroke. These conditions combined are the leading cause of morbidity and mortality in the industrialized nations.

Blood clots consist of a fibrous network that is capable of dissolution by the proteolytic enzyme plasmin. The enzyme is derived from the inactive proenzyme, plasminogen, a component of blood plasma, by the action of a plasminogen activator. There are two immunologically distinct mammalian plasminogen activators. Intrinsic plasminogen activator, also known as urokinase, is an enzyme produced by the kidney and can be isolated from urine. It can also be prepared from a number of tissue culture sources. Extrinsic plasminogen activator, also known as vascular plasminogen activator and as tissue plasminogen activator (t-PA), can be isolated from many tissue homogenates (notably human uterus), the vascular cell wall and from some cell cultures. In addition to these two kinds of plasminogen activator, there is also a bacterial product, streptokinase, prepared from beta-haemolytic streptococci. A major drawback with both urokinase and streptokinase is that they are active throughout the circulation and not just at the site of a blood clot. They can, for example, destroy other blood proteins, such as fibrinogen, prothrombin, factor V and factor VIII so reducing blood clotting ability and increasing the risk of haemorrhage. In contrast, the biological activity of t-PA is dependent on the presence of fibrin to which it binds and where it is activated. Maximum activity is thus developed only at the site of a blood clot, i.e. in the presence of the fibrin network to be dissolved, and this greatly avoids the risk of haemorrhage.

Prostaglandin $E_1$ (3-hydroxy-2-(3-hydroxy-1-octenyl)-5-oxocyclopentaneheptanoic acid) is a naturally occurring prostaglandin and was one of the first to be isolated and characterised. It is available commercially for the treatment of peripheral vascular disease.

Prostacyclin (otherwise known as epoprostenol and $PGI_2$) is also a natural prostaglandin occurring within the arterial wall of mammals. It has potent vasodilatory and antiplatelet properties and is available commercially as its sodium salt, sodium epoprostenol, for use in extracorporeal circuits during cardiopulmonary bypass, renal dialysis, and charcoal haemoperfusion. A number of recent publications in the literature have suggested that prostacyclin may also have fibrinolytic activity (*J. Pharmac. Exp. Therap.* 1982, 222(3), 544 to 549 and *Thrombos, Res.*, 1983, 29, 655 to 660). Similar reports have also occurred for the prostacyclin analogue, iloprost (*Brit. J. Pharmac.*, 1985, 86, 8138 and *Thromb. Haemost.*, 1983, 50, 893). It has also been suggested that prostacyclin augments the thrombolytic activity of streptokinase (*J. Cardiovasc. Pharmac.*, 1985, 7, 739 to 746).

A number of prostacyclin analogues have also been synthesised and evaluated as antithrombotic or antiplatelet agents (*Circulation*, 1985, 72(6), 1219 to 1225 and *Progress in Medicinal Chemistry*, 1984, 21, 237 to 279).

It has now been found that a combination of t-PA and a prostaglandin has thrombolytic activity and that the level of this activity is significantly potentiated compared with that provided by t-PA or the prostaglandin per se. Accordingly the present invention provides a combination of t-PA and a prostaglandin which is $PGE_1$, or a pharmaceutically acceptable salt thereof, or a compound of formula (I).

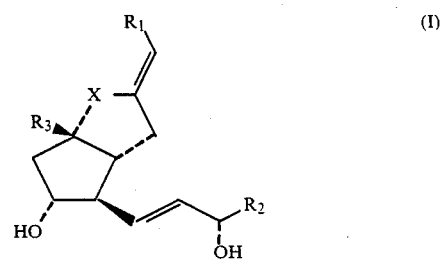

wherein $R_1$ is a $-(CH_2)_3COR_4$ or

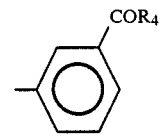

in which $R_4$ is hydroxy, $C_{1-4}$ alkoxy, amino, $C_{1-4}$ alkylamino or di-$C_{1-4}$ alkylamino, $R_2$ is n-pentyl, cyclopentyl, cyclohexyl or 1-methyl-3-pentynyl, $R_3$ is hydrogen or methyl, and X is oxygen or methylene, or a pharmaceutically acceptable salt thereof.

The present invention may be used to remove a blood clot and also to prevent formation of a clot in a patient where this is likely to occur, for example following recanalization of a blood vessel of a patient. Although the present invention may be used to remove or prevent formation of a clot in any blood vessel, it is particularly useful in removing or preventing the formation of a coronary clot.

The t-PA of use with the present invention may be any bioactive prtien substantially corresponding to mammalian, and especially human, t-PA and includes forms with and without glycosylation. It may be one- or two-chain t-PA, or a mixture thereof, as described in EP-A-112, and, in the case of fully glycosylated human t-PA, has an apparent molecular weight on polyacrylamide gel of about 70,000 and an isoelectric point of between 7.5 and 8.0. Preferably the t-PA has a specific activity of about 500,000 IU/mg (International Units/mg, the International Unit being a unit of activity as defined by WHO, National Institute for Biological Standards and Control, Holly Hill, Hampstead, London, NW3 6RB, U.K.).

The amino acid sequence of t-PA preferably substantially corresponds to that set forth in FIG. 1. The sequence is thus identical to that in FIG. 1 or contains one or more amino acid deletions, substitutions, insertions, inversions or additions of allelic origin or otherwise, the resulting sequence having at least 80%, and preferably 90%, homology with the sequence in FIG. 1 and retaining essentially the same biological and immunological properties of the protein. In particular, the sequence is identical to that in FIG. 1 or has the same sequence but with the amino acid in the 245th position from the serine N-terminus being valine instead of methionine, either sequence optionally being without any of the first three amino acids or optionally having an additional polypeptide N-terminal presequence of Gly-Ala-Arg.

The amino acid sequence set forth in FIG. 1 has thirty-five cysteine residues and thus the potential for forming seventeen disulphide bridges. Based on analogy with other proteins whose structure has been determined in more detail, the postulated structure for the sequence (arising from disulphide bond formation) between the amino acid in the 90th position and the proline C-terminus is set forth in FIG. 2. The structure of the N-terminal region is less certain although some proposals have been put forward (*Progress in Fibrinolysis*, 1983, 6, 269–273; and *Proc. Natl. Acad. Sci.*, 1984, 81, 5355–5359). The most important features of the structure of t-PA are the two kringle regions (between the 92nd and the 173rd amino acids and between the 180th and 261st amino acids), which are responsible for the binding of the protein to fibrin, and the serine protease region, which comprises the major part of the B-chain and which is responsible for the activation of plasminogen. The amino acids of special significance in serine proteases are the catalytic triad, His/Asp/Ser. In t-PA these occur at the 322nd, the 371st and the 463rd positions. The disulphide bridge between the 264th and 395th cystein amino acid residues is also important in that it holds together the A- and B-chains in the two-chain form of t-PA.

In FIGS. 1 and 2, the conventional one and three letter codes have been employed for the amino acid residues as follows:

| Asp | D | Aspartic acid | Cys | C | Cysteine | Arg | R | Arginine |
|---|---|---|---|---|---|---|---|---|
| Thr | T | Threonine | Val | V | Valine | Lys | K | Lysine |
| Ser | S | Serine | Ile | I | Isoleucine | Trp | W | Tryptophan |
| Glu | E | Glutamic acid | Leu | L | Leucine | Gln | Q | Glutamine |
| Pro | P | Proline | Tyr | Y | Tyrosine | Met | M | Methionine |
| Gly | G | Glycine | Phe | F | Phenylalanine | Asn | N | Asparagine |
| Ala | A | Alanine | His | H | Histidine | | | |

The t-PA may be obtained by any of the procedures described or known in the art. For example, it may be obtained from a normal or neoplastic cell line of the kind described in *Biochimica et Biophysica Acta*, 1979, 580, 140–153; EP-A-41 766 or EP-A-113 319. It is preferred, however, that t-PA is obtained from a cultured transformed or transfected cell line derived using recombinant DNA technology as described in, for example, EP-A-93 619; EP-A-117 059; EP-A-117 060; EP-A-173 552; EP-A-174 835; EP-A-178 105; EP-A-225 177; EP-A-225 286; WO 86/01538; WO 86/05514; or WO 86/05807. It is particularly preferred that Chinese hamster ovary (CHO) cells are used for the production of t-PA and are derived in the manner as described in *Molecular and Cellular Biology*, 1985, 5(7), 1750–1759. In this way, the cloned gene is contransfected with the gene encoding dihydrofolate reductase (dhfr) into dhfr− CHO cells. Transformants expressing dhfr are selected on media lacking nucleosides and are exposed to increasing concentrations of methotrexate. The dhfr and t-PA genes are thus coamplified leading to a stable cell line capable of expressing high levels of t-PA.

The t-PA is, preferably, purified using any of the procedures described or known in the art, such as the procedures described in *Biochimica et Biophysica Acta*, 1979, 580, 140–153; *J. Biol. Chem.*, 1979, 254(6), 1998–2003; ibid, 1981, 256(13), 7035–7041; *Eur. J. Biochem.*, 1983, 132, 681–686; EP-A-41 766; EP-A-113 319; or GB-A-2 122 219.

A preferred sub-class of prostaglandins of use with the present invention includes $PGE_1$, or a pharmaceutically acceptable salt thereof, or a compound of formula (I), wherein $R_1$, $R_2$, $R_3$ and X are as defined hereinbefore and $R_4$ is hydroxy, or a pharmaceutically acceptable salt thereof.

Examples of a pharmaceutically acceptable salt include alkali and alkaline earth metal salts. The most preferred example is the sodium salt.

Specific examples of particularly preferred prostaglandins of use with the present invention include $PGE_1$, or a pharmaceutically acceptable salt thereof, or one of the following compounds of formula (I), wherein;

1. $R_1$ is $—(CH_2)_3COR_4$ in which $R_4$ is hydroxy, $R_2$ is n-pentyl, $R_3$ is hydrogen, and X is oxygen (prostacyclin);
2. $R_1$ is $—(CH_2)_3COR_4$ in which $R_4$ is hydroxy, $R_2$ is n-pentyl, $R_3$ is hydrogen, and X is methylene (carbacyclin);
3. $R_1$ is $—(CH_2)_3COR_4$ in which $R_4$ is hydroxy, $R_2$ is n-pentyl, $R_3$ is methyl, and X is methylene (9-β-methylcarbacyclin);
4. $R_1$ is $—(CH_2)_3COR_4$ in which $R_4$ is hydroxy, $R_2$ is 1-methyl-3-pentynyl, $R_3$ is hydrogen, and X is methylene (iloprost);
5. $R_1$ is $—(CH_2)_3COR_4$ in which $R_4$ is hydroxy, $R_2$ is cyclopentyl, $R_3$ is hydrogen and x is methylene;
6. $R_1$ is

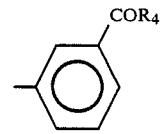

in which $R_4$ is hydroxy, $R_2$ is cyclohexyl, $R_3$ is hydrogen, and X is methylene; or a pharmaceutically acceptable salt thereof.

The prostaglandin of use with the present invention may be prepared and purified by any suitable process described or known in the art, for example *J. Am. Chem. Soc.*, 1969, 91, 535; British Pat. No. 1 583 961; GB-A 2 012 265; GB-A 2 013 661; GB-A 2 017 699; GB-A 2 070 596; U.S. Pat. No. 4 238 414; EP-A 105 651; EP-A 134 153; EP-A 153 822; WO 86/00808; U.S. Pat. No. 4,510,323; U.S. Pat. No. 4,349,689; and U.S. Pat. No. 4,420,632.

In using t-PA and a prostaglandin in the manner of the present invention, it is preferred to employ them in the form of a pharmaceutical formulation. The active ingredients may be employed in separate formulations or in a single combined formulation although in the latter formulation both active ingredients must of course be stable and mutually compatible in the particular formulation employed. The present invention also therefore provides a pharmaceutical formulatoin, which comprises t-PA and a prostaglandin, as defined hereinbefore, and a pharmaceutically acceptable carrier.

Generally, t-PA and the prostaglandin will be administered by the intravascular route, whether by infusion or by bolus injection, and thus a parenteral formulation is required. It is preferred to present a lyophilised formulation to the physician or veterinarian because of the significant transportation and storage advantages that it affords. The physician or veterinarian may then reconstitute the lyophilised formulation in an appropriate amount of solvent as and when required.

Parenteral and lyophilised pharmaceutical formulations containing t-PA are known in the art. Examples of such art include EP-A-41 766; EP-A-93 619; EP-A-112 122; EP-A-113 319; EP-A-123 304; EP-A-143 081; EP-A-156 169; EP-A-211 592; EP-A-217 379; EP-A-218 112; WO86/01104; Japanese patent publication No. 57-120523 (application 56-6936) and Japanese patent publication 58-65218 (application 56-163145). Additional examples include GB-A-2 176 702; GB-A-2 176 703 and GB-A-2 184 354.

Parenteral and lyophilised formulations containing a prostaglandin, as defined hereinbefore, are also known in the art. Examples of such art include the aforementioned British patent specifications and also EP-A-5 768.

Parenteral and lyophilised formulations containing t-PA and the prostaglandin together in a single, combined formulation may be prepared in a similar manner to the preparation of formulations suitable for t-PA or the prostaglandin per se. As mentioned before, however, the stability and mutual compatibility of the active ingredients in a particular formulation will need to be taken into account and the formulation adapted accordingly.

Intravascular infusions are normally carried out with the parenteral solution contained within an infusion bag or bottle or within an electrically operated infusion syringe. The solution may be delivered from the infusion bag or bottle to the patient by gravity feed or by the use of an infusion pump. The use of gravity feed infusion systems does not afford sufficient control over the rate of administration of the parenteral solution and, therefore, the use of an infusion pump is preferred especially with solutions containing relatively high concentrations of active ingredients. More preferred, however, is the use of an electrically operated infusion syringe which offers even greater control over the rate of administration.

The present invention also provides a method for removing or inhibiting the formation of a blood clot in a mammal, which comprises administering to the mammal an effective amount of t-PA and a prostaglandin, as defined hereinbefore. In the alternative, the present invention provides a combination of t-PA and a prostaglandin, as defined hereinbefore, for use in human and veterinary medicine especially for use in removing or inhibiting the formation of a blood clot in a mammal.

In using t-PA and a prostaglandin in the manner of the present invention, the active ingredients may be administered concurrently or sequentially as separate formulations or as a single combined formulation. If there is sequential administration, the delay in administering the second of the active ingredients should not be such as to lose the benefit of a potentiated thrombolytic or anti-thrombotic effect of the combination of the active ingredients.

An effective amount of t-PA and a prostaglandin to remove or inhibit the formation of a blood clot in a mammal will of course depend upon a number of factors including, for example, the age and weight of the mammal, the precise condition requiring treatment and its severity, the route of administration, the particular form of t-PA and prostaglandin employed and their potency, and will ultimately be at the discretion of the attendant physician or veterinarian. It is likely, however, that an effective amount, in the case of t-PA, will be from 14,000 to 400,000 IU per kg per hour, and, in the case of the prostaglandin, will be from 30 to 30,000 ng per kg per hour; for example in the case of prostacyclin an effective amount will probably be from 120 to 960 ng per kg per hour. Thus, for a 70kg adult human being, an effective amount per hour will generally be, in the case of t-PA, from 1,000,000 to 25,000,000 IU, and, in the case of the prostaglandin, from 2100 to 2,100,000ng.

The following examples are provided in illustration of the present invention and should not be construed in any way as constituting a limitation thereof.

EXAMPLE 1

The thrombolytic efficacy of t-PA, prostacyclin and a combination thereof was evaluated in an in vivo model of jugular vein thrombosis.

METHODOLOGY

Anaesthesia was induced in the rabbit with an intravenous injection of sodium pentobarbitone (30mg/kg). A constant level of anaesthesia was maintained for the duration of the experiment by intravenous infusion as needed of a dilute sodium pentobarbitone solution (1 mg/ml). A 10 cm ventral midline incision in the cervical region was made to expose the trachea and the left external jugular vein. A tracheal tube was inserted and the animal artificially ventilated (40 bpm, 18 ml tidal volume) with a rodent respirator to maintain constant respiration. The femoral vein and artery was isolated and cannulated.

Cauterization was utilised to isolate a segment of the external jugular vein 2cm cephaled to the bifurcation of the facial vein and 4cm caudad (approximate distances). All venous tributaries were ligated or cauterized along the length of the exposed vein. The facial vein was cannulated with PE$_{50}$ tubing. The exposed jugular vein was clamped distal and proximal to the bifurcation to isolate a section. A suture thread (2-0 bpc, Davis and Geck, Gosport, England) was introduced longitudinally int the lumen of the isolated segment using a round bodied suture needle (gauge 4, Ethicon Ltd., Edinburgh, Scotland). Blood flow was then re-established. When bleeding ceased from the needle punctures, the jugular vein segment was re-isolated and emptied of all blood, via the facial vein cannula. The thrombus was then formed by the following procedure. Human thrombin (500 units/ml; 10 μl) was introduced into the vein segment. A volume of blood equivalent to the isolated segment capacity was withdrawn from the femoral artery and added to a 12×75 mm test tube containing 10 μl (−1,900,000 dpm) of $^{125}$I-labelled human fibrinogen (Amersham International p.l.c., England). The blood was aspirated into a 1 ml syringe for the subsequent injection through the facial vein catheter into the isolated vein segment. Any remaining blood in the facial vein catheter was flushed down with saline. Occlusive clots were formed quickly and allowed to age for 30 minutes. At this time, blood flow was re-established through the vein segment by the removal of the clamps. Thyroidal uptake of radioiodide was blocked by a 1 ml intravenous injection of a 2% (w/v) sodium iodide (Mallinkrodt, Paris, KY) solution prior to thrombus formation.

The t-PA was obtained from a cultured transfected CHO cell line that had been derived using the procedure of *Molecular and Cellular Biology,* 1985, 5(7), 1750–1759, purified, and formulated as an aqueous saline solution at pH 3, as described in GB-A-2176703. This solution was infused (24ml) via a femoral vein over a 2 hour period following a loading bolus in a dose of 1 ml over the first minute.

The prostacyclin was prepared as the sodium salt using the procedure of British Pat. No. 1 583 961, dissolved in 1M Tris buffer (pH 9.6 at 4° C.) and diluted with isotonic sodium bicarbonate solution (1.25% w/v, pH 8.6, 4° C.). This solution, which is described in EP-A-5 768, was infused intravenously, either via the femoral vein or locally into the ear vein, for the 2 hour period.

RESULTS

Figure 3:
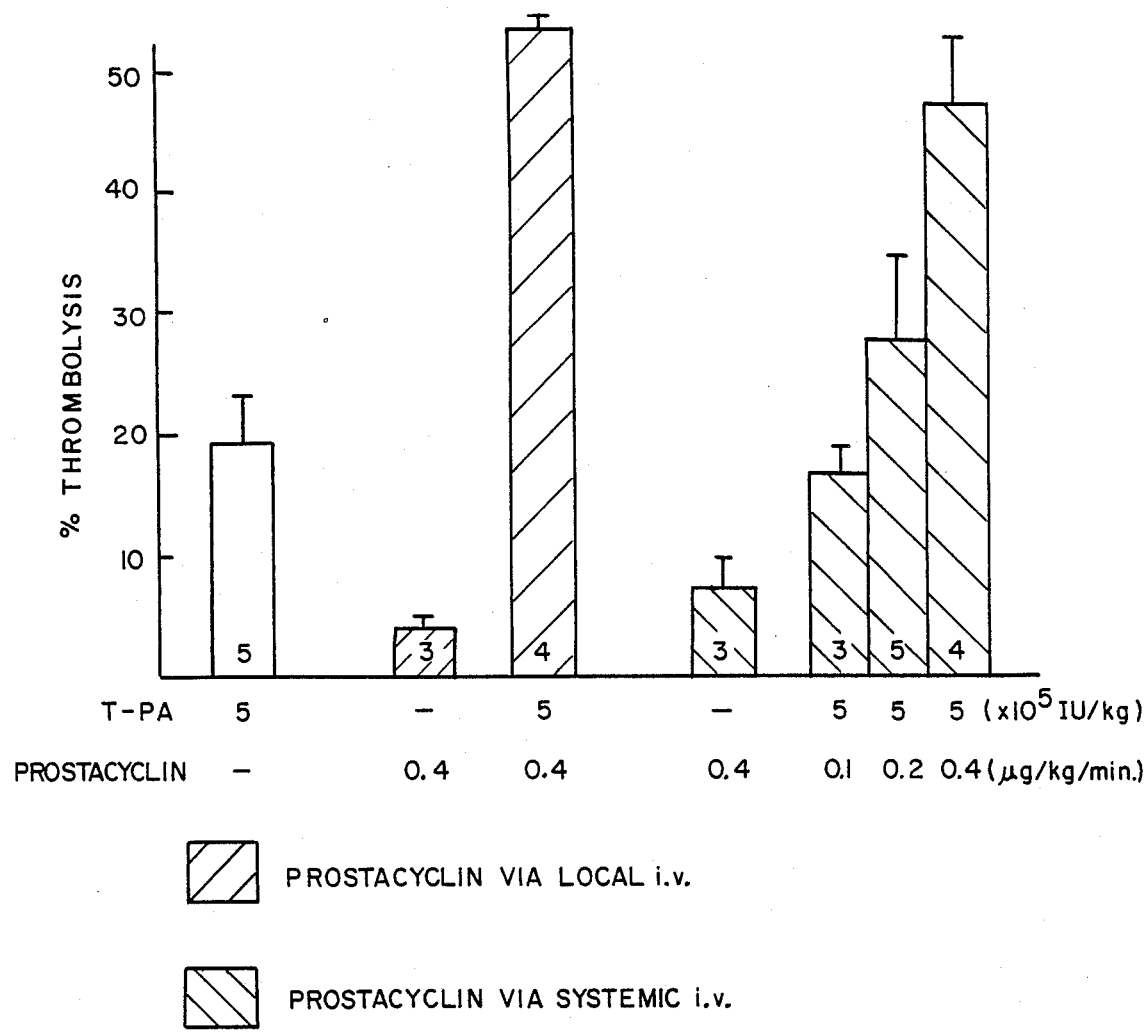

Intravenous infusion of t-PA caused a dose-related thrombolysis in this model. Intravenous infusion of prostacyclin (0.1–0.4 µg kg$^{-1}$ min $^{-1}$), either systemically or locally did not induce a significant degree of thrombolysis. However, local intravenous infusion of prostacyclin (0.4 µg kg$^{-1}$ min$^{-1}$) significantly (p<0.001) potentiated the thrombolytic action of a submaximal dose of t-PA (5×10$^5$ IU kg$^{-1}$). Likewise, systemic intravenous infusion of prostacyclin (0.1–40 µg kg$^{-1}$ min$^{-1}$) caused a dose-related increase in thrombolysis induced by t-PA (5×10$^5$ IU kg$^{-1}$), with the highest dose of prostacyclin inducing significant (p<0.01) potentiation of this response. The results are represented pictorially in FIG. 3.

I claim:

1. A method of removing a blood clot in a mammal in need thereof comprising the parenteral administration to said mammal of t-PA and prostacyclin or a pharmaceutically acceptable salt thereof, wherein said t-PA and prostacyclin or said pharmaceutically acceptable salt thereof are administered in amounts to provide a synergistic effect.

2. The method according to claim 1 in which the prostacyclin or salt thereof and t-PA are administered concurrently.

3. The method according to claim 1 in which the prostacyclin or salt thereof and t-PA are administered sequentially.

4. A method of removing a blood clot in a mammal in need thereof comprising the parenteral administration to said mammal of t-PA and a compound of formula (I), said t-PA and a compound of formula (I),

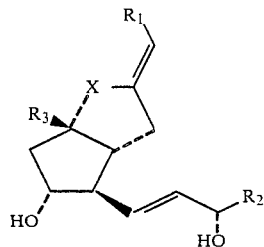

wherein R$_1$ is —(CH$_2$)$_3$COR$_4$ or

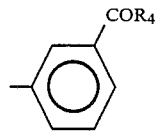

in which R$_4$ is hydroxy, C$_{1-4}$ alkoxy, amino, C$_{1-4}$ alkylamino or di-C$_{1-4}$ alkylamino, R$_2$ is n-pentyl, cyclopentyl, cyclohexyl or 1-methyl-3-pentynyl, R$_3$ is hydrogen or methyl, and X is oxygen, or a pharmaceutically acceptable salt thereof, wherein said compound of formula (I) or said pharmaceutically acceptable salt thereof and t-PA are administered in amounts to provide a synergistic effect.

5. The method according to claim 4 in which the compound of formula I or salt thereof and t-PA are administered concurrently.

6. The method according to claim 4 in which the compound of formula (I) or salt thereof and t-PA are administered sequentially.

7. A method of removing a blood clot in a mammal in need thereof comprising the parenteral administration to said mammal of t-PA and a compound of formula (I),

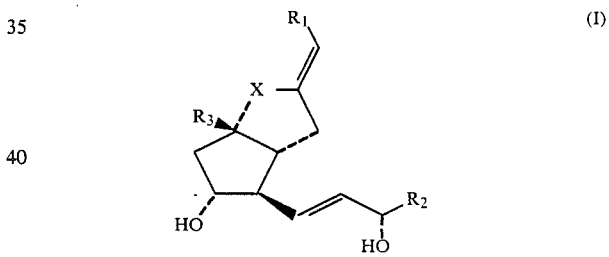

wherein R$_1$ is —(CH$_2$)$_3$COR$_4$ or

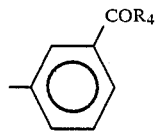

in which R$_4$ is hydroxy, C$_{1-4}$ alkoxy, amino, C$_{1-4}$ alkylamino or di-C$_{1-4}$ alkylamino, R$_2$ is n-pentyl, cyclopentyl, cyclohexyl or 1-methyl-3-pentynyl, R$_3$ is hydrogen or methyl, and X is methylene, or a pharmaceutically acceptable salt thereof, wherein said t-PA and the compound of formula (I) or said pharmaceutically acceptable salt thereof are administered in amounts to provide a synergistic effect.

8. The method according to claim 7 in which the compound of formula I or salt thereof and t-PA are administered concurrently.

9. The method according to claim 8 in which the compound or salt thereof and t-PA are administered sequentially.

10. The method of claim 7 in which the compound of R is —(CH$_2$)$_3$COR$_4$ in which R$_4$ is hydroxy, R$_2$ is 1-methyl-3-pentynyl, R$_3$ is hydrogen.

11. The method of claim 7 in which R$_1$ is (CH$_2$)$_3$COR$_4$ in which R$_4$ hydroxy, R$_2$ in n-pentyl and R$_3$ is hydrogen.

* * * * *